United States Patent
Yamazaki et al.

(10) Patent No.: US 10,273,200 B2
(45) Date of Patent: Apr. 30, 2019

(54) PRACTICAL METHOD FOR MANUFACTURING 3,3-DIFLUORO-2-HYDROXYPROPIONIC ACID

(71) Applicant: Central Glass Company, Limited, Ube-shi, Yamaguchi (JP)

(72) Inventors: Takako Yamazaki, Kawagoe (JP); Ryuichi Okamoto, Kawagoe (JP); Akihiro Ishii, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 15/551,640

(22) PCT Filed: Mar. 15, 2016

(86) PCT No.: PCT/JP2016/058056
§ 371 (c)(1),
(2) Date: Aug. 17, 2017

(87) PCT Pub. No.: WO2016/158365
PCT Pub. Date: Oct. 6, 2016

(65) Prior Publication Data
US 2018/0037533 A1   Feb. 8, 2018

(30) Foreign Application Priority Data

Mar. 27, 2015 (JP) ................ 2015-066966

(51) Int. Cl.
| C07C 45/67 | (2006.01) |
| C07C 49/16 | (2006.01) |
| C07C 51/295 | (2006.01) |
| C07C 59/115 | (2006.01) |
| C07C 67/307 | (2006.01) |
| C07C 69/716 | (2006.01) |

(52) U.S. Cl.
CPC .......... *C07C 67/307* (2013.01); *C07C 45/676* (2013.01); *C07C 51/295* (2013.01); *C07C 69/716* (2013.01)

(58) Field of Classification Search
CPC ... C07C 45/676; C07C 51/295; C07C 67/307; C07C 69/716
See application file for complete search history.

(56) References Cited

U.S. PATENT DOCUMENTS

| 4,713,485 A | 12/1987 | Andre et al. |
| 2004/0049076 A1 | 3/2004 | Ishii et al. |
| 2008/0114196 A1 | 5/2008 | Kutschera et al. |
| 2015/0284368 A1 | 10/2015 | Kuduk et al. |

FOREIGN PATENT DOCUMENTS

| CN | 101429083 A | 5/2009 |
| CN | 103570533 A | 2/2014 |
| GB | 1 560 186 A | 1/1980 |
| JP | 53-130620 A | 11/1978 |
| JP | 61-191648 A | 8/1986 |
| JP | 9-227440 A | 9/1997 |
| JP | 09227440 * | 9/1997 |
| JP | 2004-18503 A | 1/2004 |
| JP | 2007-39384 A | 2/2007 |
| JP | 2008-120802 A | 5/2008 |
| JP | 2015-204762 A | 11/2015 |
| WO | WO 2014/078220 A1 | 5/2014 |

OTHER PUBLICATIONS

English translation of JP09227440, pp. 1-5, Sep. 2, 1997.*
Yasumoto et al., "Self-disproportionation of enantiomers of isopropyl 3,3,3-trifluoro lactate via sublimation: Sublimation rates vs. enantiomeric composition," Journal of Fluorine Chemistry, 131 (2010) 535-539.*
Takahaski et al., "Isomorphic supramolecular structures via one-dimensional hydrogen bonding motifs in crystals of chiral difluorolactates, trichlorolactates and trifluorolactates," CrystEngComm, 2006, pp. 320-326.*
International Search Report (PCT/ISA/210) issued in PCT Application No. PCT/JP2016/058056 dated Jun. 14, 2016 with English translation (5 pages).
Japanese-language Written Opinion (PCT/ISA/237) issued in PCT Application No. PCT/JP2016/058056 dated Jun. 14, 2016 (5 pages).
Takahashi et al., "Isomorphic Supramolecular Structures via One-Dimensional Hydrogen Bonding Motifs in Crystals of Chiral Difluorolactates, Trichlorolactates and Trifluorolactates", CrystEngComm, 2006, pp. 320-326, vol. 8. (Sixteen (16) pages total).
Sevenard et al., "Halogenation of Fluorinated Cyclic 1,3-Dicarbonyl Compounds: New Aspects of Synthetic Application", Tetrahedron, 2009, pp. 7538-7552, vol. 65.
McBee et al., "The Preparation and Reactions of Fluorine-Containing Acetoacetic Esters", Journal of American Chemical Society, Jul. 5, 1953, pp. 2152-2153, vol. 75.
Japanese-language Office Action issued in counterpart Japanese Application No. 2015-066966 dated Aug. 7, 2018 with English translation (seven (7) pages).

* cited by examiner

*Primary Examiner* — Pancham Bakshi
*Assistant Examiner* — Mark R Luderer
(74) *Attorney, Agent, or Firm* — Crowell & Moring LLP

(57) ABSTRACT

Disclosed is a practical method for production of 3,3-difluoro-2-hydroxypropionic acid, which is important as pharmaceutical and agrichemical intermediates. The method includes forming a 4,4-difluoro-2,2-dichloro-3-oxobutanoic acid ester by reaction of a 4,4-difluoro-3-oxobutanoic acid ester with chlorine ($Cl_2$), forming 3,3-difluoro-1,1-dichloro-2-propanone by reaction of the chlorination product with an acid, and then, reacting the degradation product with a basic aqueous solution.

6 Claims, No Drawings

PRACTICAL METHOD FOR MANUFACTURING 3,3-DIFLUORO-2-HYDROXYPROPIONIC ACID

FIELD OF THE INVENTION

The present invention relates to a practical method for production of 3,3-difluoro-2-hydroxypropionic acid.

BACKGROUND ART

It is known that 3,3-difluoro-2-hydroxypropionic acid is an important compound as pharmaceutical and agrichemical intermediates. For example, 3,3-difluoro-2-hydroxypropionic amide, which is easily derived from this acid compound, is used as intermediates for production of phosphodiesterase 10 inhibitors (see Patent Document 1).

Typically known is a method of producing 3,3-difluoro-2-hydroxypropionic acids by oxidation decomposition of furan skeletons (see Non-Patent Document 1).

As a conventional technique relevant to a chlorination step of the present invention, there is known a method of producing 4,4,4-trifluoro-2,2-dichloro-3-oxobutanoic acid ester from 4,4,4-trifluoro-3-oxobutanoic acid ester (see Patent Document 2 and Non-Patent Document 2).

As a conventional technique relevant to a degradation step of the present invention, there is known a method of producing 3,3,3-trifluoro-1,1-dichloro-2-propanone from 4,4,4-trifluoro-2,2-dichloro-3-oxobutanoic acid ester (see Patent Document 2).

There is further known, as a conventional technique relevant to an alkali decomposition step of the present invention, a method of producing 3,3,3-trifluoro-2-hydroxypropionic acid from 3,3,3-trifluoro-1,1-dichloro-2-propanone (see Patent Document 3).

PRIOR ART DOCUMENTS

Patent Documents

Patent Document 1: International Publication No. 2014-078220
Patent Document 2: Japanese Laid-Open Patent Publication No. H9-227440
Patent Document 3: Japanese Laid-Open Patent Publication No. 2004-018503

Non-Patent Documents

Non-Patent Document 1: Cryst. Eng. Comm. (U.K.), 2006, vol. 8, p. 320-326
Non-Patent Document 2: Tetrahedron (Netherlands), 2009, vol. 65, p. 7538-7552

SUMMARY OF THE INVENTION

Problems to be Solved by the Invention

The production method of Non-Patent Document 1 involves a long process of reaction steps and thus is not practical.

It is an object of the present invention to provide a practical method by which 3,3-difluoro-2-hydroxypropionic acid, important as pharmaceutical and agrichemical intermediates, can be produced with high productivity under industrially applicable mild reaction conditions through a shorter process than those in the conventional method.

Means for Solving the Problems

As a result of extensive researches made to achieve the above object, the present inventors have newly found that it is possible to produce 3,3-difluoro-2-hydroxypropionic acid by reacting a 4,4-difluoro-3-oxobutanoic acid ester with chloride gas to form a 4,4-difluoro-2,2-dichloro-3-oxobutanoic acid ester, reacting the thus-formed ester with an acid to form 3,3-difluoro-1,1-dichloro-2-propanone, and then, reacting the thus-formed propanone with a basic aqueous solution. Accordingly, the production method of the present invention includes three steps: a first step of chlorination, a second step of degradation and a third step of alkali decomposition as shown in Scheme 1. The present inventors have also newly found a 4,4-difluoro-2,2-dichloro-3-oxobutanoic acid ester, which is a novel compound useful as an intermediate in the production method of the present invention.

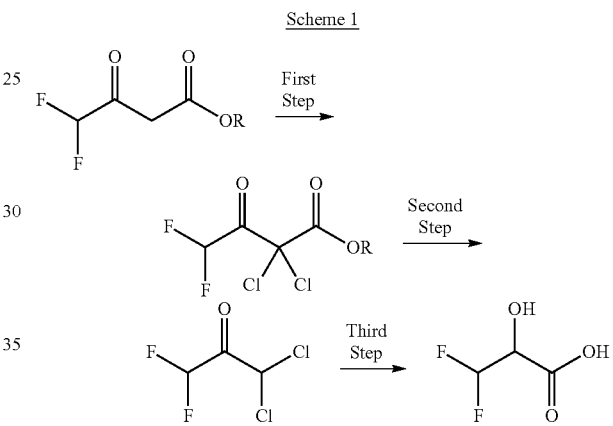

Scheme 1

In comparison to Patent Documents 2 and 3 and Non-Patent Document 2, there are chemically expected problems in the respective steps of the present invention.

In Patent Document 2, the chlorination step adopts severe reaction conditions and causes significant chlorination of the ester moiety as a side reaction (see the following formula). The raw substrate material of the present invention, that is, 4,4-difluoro-3-oxobutanoic acid ester has a hydrogen atom at its 4-position. As is known, α-proton of carbonyl can be easily halogenated. It is generally conceivable that, when the reaction conditions of Patent Document 2 are simply adopted, the raw substrate material of the present invention will be chlorinated at not only the ester moiety but also the 4-position. Further, the occurrence of the side reaction leads to an increase in the amount of chlorine gas used in the chlorination step. The industrial application of such a chlorination step is not favorable in terms of cost and chlorine waste disposal. As a natural consequence, the operations for purification of the target compound becomes complicated.

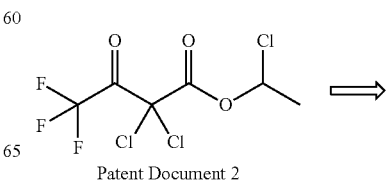

Patent Document 2

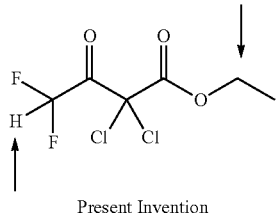

Present Invention

In Patent Document 2, the degradation step also adopts severe reaction conditions. In the industrial application of such a degradation step, there arise problems of limitation of material against high-temperature conditions and large amount of sulfuric acid waste disposal.

In Non-Patent Document 2, the chlorination step uses a large excess of relatively expensive sulfuryl chloride as the chlorination agent and shows a medium level of yield even after a long time of reaction. The chlorination step further uses diethyl ether, which is a special inflammable material, as the reaction solvent in Non-Patent Document 2.

In Patent Document 3,3,3,3-trifluoro-1,1-dichloro-2-propanone is used as the raw substrate material, which is apparently different in structural features from the target 3,3-difluoro-1,1-dichloro-2-propanone of the present invention (see below). By comparison of substituents on both sides of the carbonyl group, it is clear which part of the substrate material of Patent Document 3 will undergo alkali decomposition ($CF_3$ group<$CHCl_2$ group). On the other hand, dihalogenated methyl groups are present on both sides of the carbonyl group in the target substrate material of the present invention. It is expected that the respective dihalogenated methyl groups will undergo alkali decomposition ($CHF_2$ group =$CHCl_2$ group). In other words, there is a possibility of formation of 3,3-difluoro-2-hydroxypropionic acid and 3,3-dichloro-2-hydroxypropionic acid from the substrate material of the present invention. It has totally been unknown whether desired regioselectivity (functional group selectivity) can be obtained in the alkali decomposition reaction (i.e. whether alkali decomposition of dichloromethyl group will proceed preferentially).

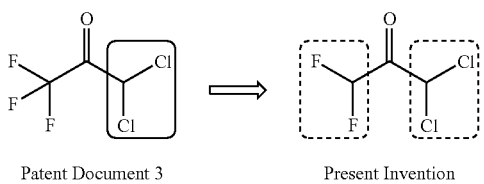 [SMILES: O=C(C(Cl)Cl)C(F)(F)F ; O=C(C(F)F)C(Cl)Cl]

Patent Document 3      Present Invention

Contrary to the above expectations, the respective steps of the present invention proceed with high regioselectivity and high conversion rate under the conditions adopted by the present inventors.

In the chlorination step of the present invention, it is possible to improve the efficiency of use of chlorine ($Cl_2$) by reacting the target substrate with chlorine in the presence of water. In particular, it is possible to further improve the efficiency of use of chlorine by performing the monochlorination in the absence of water and then performing the dichlorination in the presence of water. The chlorination step of the present invention can be conducted with a small excess of chlorine, which is the most inexpensive chlorination agent, and achieves a short reaction time and high reaction yield. In addition, there is no need to use a reaction solvent unsuitable for industrial applications.

In the degradation step of the present invention, it is possible to adopt the mild reaction conditions by reacting the chlorination product with an acidic aqueous solution. It is particularly possible to lower the reaction temperature and reduce the amount of the acid used. There can be thus avoided the problems of material limitation and large amount of acid waste disposal in industrial applications.

In the alkali decomposition step of the present invention, it is possible to produce the target 3,3-difluoro-2-hydroxypropionic acid with desired regioselectivity by reacting the degradation product with the basic aqueous solution.

There has been known no method for selective production of the 3,3-difluoro-1,1-dichloro-2-propanone as the substrate material of the present invention. Moreover, the 4,4-difluoro-2,2-dichloro-3-oxobutanoic acid ester is a novel compound and has not been known to be an intermediate useful for practical production of the 3,3-difluoro-2-hydroxypropionic acid.

The specific reaction conditions of the present invention are preferred embodiments for production of the 3,3-difluoro-2-hydroxypropionic acid.

Namely, the present invention includes the following inventive aspects 1 to 5.

Inventive Aspect 1

A method for producing 3,3-difluoro-2-hydroxypropionic acid of the formula [4]

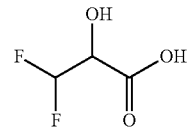

[4]

the method comprising the following steps:
[first step] reacting a 4,4-difluoro-3-oxobutanoic acid ester of the general formula [1] with chlorine ($Cl_2$), thereby forming a 4,4-difluoro-2,2-dichloro-3-oxobutanoic acid ester of the general formula [2]

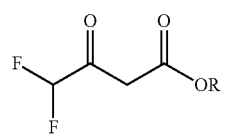

[1]

where R is a $C_1$-$C_6$ alkyl group;

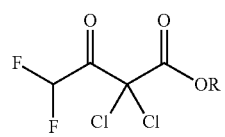

[2]

where R is a $C_1$-$C_6$ alkyl group;
[second step] reacting the 4,4-difluoro-2,2-dichloro-3-oxobutanoic acid ester formed in the first step with an acid, thereby forming 3,3-difluoro-1,1-dichloro-2-propanone of the formula [3]

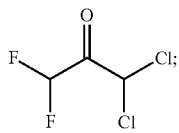

[3]

and

[third step] reacting the 3,3-difluoro-1,1-dichloro-2-propanone formed in the second step with a basic aqueous solution to obtain the 3,3-difluoro-2-hydroxypropionic acid of the formula [4].

Inventive Aspect 2

The method according to Inventive Aspect 1, wherein the 4,4-difluoro-3-oxobutanoic acid ester is reacted with chlorine ($Cl_2$) (first step) in the presence of water.

Inventive Aspect 3

The method according to Inventive Aspect 1, wherein the first step includes: converting the 4,4-difluoro-3-oxobutanoic acid ester of the general formula [1] to a 4,4-difluoro-2-chloro-3-oxobutanoic acid ester of the general formula [5] by reaction with chlorine ($Cl_2$) in the absence of water; and then, converting the 4,4-difluoro-2-chloro-3-oxobutanoic acid ester to the 4,4-difluoro-2,2-dichloro-3-oxobutanoic acid ester of the general formula [2] by reaction with chlorine ($Cl_2$) in the presence of water

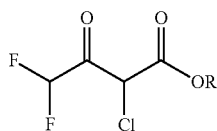

[5]

where R is a $C_1$-$C_6$ alkyl group.

Inventive Aspect 4

The method according to any one of Inventive Aspects 1 to 3, wherein the acid used in the second step is an acidic aqueous solution.

Inventive Aspect 5

A 4,4-difluoro-2,2-dichloro-3-oxobutanoic acid ester of the general formula [2]

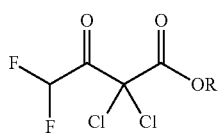

[2]

where R is a $C_1$-$C_6$ alkyl group.

Although there has not been known a production method of 3,3-difluoro-1,1-dichloro-2-propanone itself, it has been found in the present invention that: 3,3-difluoro-1,1-dichloro-2-propanone can be easily produced from a novel 4,4-difluoro-2,2-dichloro-3-oxobutanoic acid ester compound; and the alkali decomposition of the thus-obtained 3,3-difluoro-1,1-dichloro-2-propanone proceeds with desired regioselectivity. Based on these findings, it becomes possible for the first time to produce 3,3-difluoro-2-hydroxypropionic acid through a short process.

As mentioned above, the present invention enables high-productivity production of the 3,3-difluoro-2-hydroxypropionic acid, which is important as pharmaceutical and agrichemical intermediates, under industrially applicable mild reaction conditions through a short process. The problems of the conventional techniques are highly solved by the present invention. The practical production method of the 3,3-difluoro-2-hydroxypropionic acid according to the present invention is therefore significantly advantageous over the conventional techniques.

DETAILED DESCRIPTION OF THE EMBODIMENTS

Hereinafter, the present invention will be described in detail below by explaining the respective chlorination, degradation and alkali decomposition steps.

1. First Step (Chlorination Step)

In the first step, the 4,4-difluoro-2,2-dichloro-3-oxobutanoic acid ester of the general formula [2] is formed by reacting the 4,4-difluoro-3-oxobutanoic acid ester of the general formula [1] with the chlorine.

In the 4,4-difluoro-3-oxobutanoic acid ester of the general formula [1], R is a $C_1$-$C_6$ alkyl group. The alkyl group can be linear, branched or cyclic (in the case of 3 or more carbons). Among others, a $C_1$-$C_4$ alkyl group is preferred. Particularly preferred are methyl and ethyl.

It is feasible to prepare the 4,4-difluoro-3-oxobutanoic acid ester of the general formula [1] with reference to e.g. Journal of American Chemical Society (U.S.), 1953, vol. 75, p. 2152-3153. Alternatively, the 4,4-difluoro-3-oxobutanoic acid ester can be provided as a commercially available product.

The amount of the chlorine used is generally 1.4 mol or more, preferably 1.6 to 5 mol, more preferably 1.8 to 3 mol, per 1 mol of the 4,4-difluoro-3-oxobutanoic acid ester of the 4,4-difluoro-3-oxobutanoic acid ester of the general formula [1].

In the first step, the efficiency of use of the chlorine can be improved by reacting the target substrate with the chlorine in the presence of water. The efficiency of use of the chlorine can be further improved by performing the monochlorination in the absence of water and then performing the dichlorination in the presence of water.

The amount of the water used is generally 0.01 L (liter) or more, preferably 0.03 to 5 L, more preferably 0.05 to 3 L, per 1 mol of the 4,4-difluoro-3-oxobutanoic acid ester of the general formula [1].

In the first step, the desired reaction can be performed smoothly in the presence of a radial initiator such as 2,2'-azobis(2-methylpropionitrile), 1,1'-azobis(cyclohexanecarbonitrile), di-tert-butyl peroxide or benzoyl peroxide, or an acid such as acetic acid, hydrogen chloride or sulfuric acid, or by irradiation with light. These conditions are not necessarily required when the preferable reaction conditions are adopted.

Examples of the reaction solvent are halogenated solvents such as methylene chloride, chloroform, carbon tetrachloride, 1,2-dichloroethane, 1,1,2,2-tetrachloroethane, 2,4-dichlorobenzotrifluoride and 1,4-bis(trifluoromethyl)benzene. Among others, chloroform, carbon tetrachloride, 1,1,2,2-tetrachloroethane and 2,4-dichlorobenzotrifluoride are preferred. Particularly preferred are carbon tetrachloride and 2,4-dichlorobenzotrifluoride. These reaction solvents can be used solely or in combination thereof. In the first step, the reaction can be performed without the use of the reaction solvent. In some cases, it may be preferable to perform the reaction in a neat condition.

The amount of the reaction solvent used is generally 0.01 L or more, preferably 0.02 to 7 L, more preferably 0.03 to 5 L, per 1 mol of the 4,4-difluoro-3-oxobutanoic acid ester of the general formula [1].

Further, the generation of a perchloride as a by-product can be effectively suppressed by adoption of the mild reaction temperature in the first step.

The reaction temperature is generally +70° C. or lower, preferably +50 to −30° C., more preferably +30 to −10° C.

The reaction time is generally 36 hours or less. Since the reaction time varies depending on the substrate material and the reaction conditions, it is preferable to determine the time at which there is seen almost no decrease of the substrate material as the end of the reaction while monitoring the progress of the reaction by any analytical means such as gas chromatography, liquid chromatography or nuclear magnetic resonance.

It is feasible to obtain the 4,4-difluoro-2,2-dichloro-3-oxobutanoic acid ester of the general formula [2] by post-treatment operation commonly used in organic synthesis. The thus-recovered crude product can be purified to a higher purity, as required, by fractional distillation, recrystallization, column chromatography etc. When the reaction is performed in the presence of water, the 4,4-difluoro-2,2-dichloro-3-oxobutanoic acid ester of the general formula [2] may be obtained as a hydrate (see below). The 4,4-difluoro-2,2-dichloro-3-oxobutanoic acid ester hydrate (gem-diol) of the general formula [2a] can be easily converted to the 4,4-difluoro-2,2-dichloro-3-oxobutanoic acid ester (carbonyl compound). This hydrate may be used as the substrate material for the subsequent step in the same manner as the anhydride. Further, the resulting reaction product may undergo the degradation reaction of the subsequent step to form 3,3-difluoro-1,1-dichloro-2-propanone of the formula [3] or its hydrate (gem-diol) of the formula [3] (see below). Thus, the present invention includes the case where the compound of the general formula [2], the formula [3] or the formula [3a] is contained in the reaction product. In terms of operation, it is convenient to purge the remaining chlorine from the reaction-completed solution by blowing nitrogen ($N_2$) etc. into the reaction-completed solution, and then, use the reaction-completed solution as the substrate material for the subsequent step. The chlorination reaction of the first step and the degradation reaction of the second step can be conducted in one-pot reaction process.

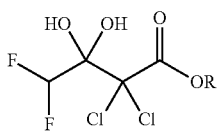

[2a]

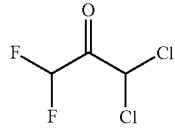

[3]

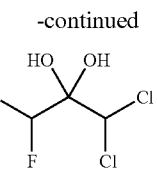

[3a]

It is understood that R of the 4,4-difluoro-2,2-dichloro-3-oxobutanoic acid ester of the general formula [2] is derived from R of the 4,4-difluoro-3-oxobutanoic acid ester of the general formula [1].

2. Second Step (Degradation Step)

In the second step, the 3,3-difluoro-1,1-dichloro-2-propanone of the formula [3] is formed by reacting the 4,4-difluoro-2,2-dichloro-3-oxobutanoic acid ester of the general formula [2] obtained in the above first chlorination step with the acid.

Examples of the acid are: inorganic acids such as boric acid, phosphoric acid, hydrogen chloride, hydrogen bromide, nitric acid and sulfuric acid; and organic acids such as formic acid, acetic acid, trifluoroacetic acid, oxalic acid, benzoic acid, methanesulfonic acid, trifluoromethanesulfonic acid, benzenesulfonic acid and p-toluenesulfonic acid. Among others, inorganic acids are preferred. Particularly preferred are hydrogen chloride and sulfuric acid.

The amount of the acid used is generally 0.01 mol or more, preferably 0.03 to 15 mol, more preferably 0.05 to 10 mol, per 1 mol of the 4,4-difluoro-2,2-dichloro-3-oxobutanoic acid ester of the general formula [2]. Hydrogen chloride remaining in the product of the previous step can be utilized as the acid in this step.

In the second step, the amount of use of the acid can be reduced by reacting the ester with an acidic aqueous solution.

The acid aqueous solution is prepared from the above acid and water. Water remaining in the product of the previous step can be utilized as the water in this step.

The concentration of the acidic aqueous solution is generally 0.1% or higher, preferably 0.3 to 90%, more preferably 0.5 to 80%.

Examples of the reaction solvent are: ether solvents such as tetrahydrofuran, 2-methyltetrahydrofuran, tert-butyl methyl ether, diisopropyl ether and 1,2-dimethoxyethane; and alcohol solvents such as methanol, ethanol, n-propanol, n-butanol and isobutanol. Among others, alcohol solvents are preferred. Particularly preferred are methanol and ethanol. These reaction solvents can be used solely or in combination thereof. In the second step, the reaction can be performed without the use of the reaction solvents. In some cases, it may be preferable to perform the reaction in a neat condition.

The amount of the reaction solvent used is generally 0.01 L or more, preferably 0.02 to 7 L, more preferably 0.03 to 5 L, per 1 mol of the 4,4-difluoro-2,2-dichloro-3-oxobutanoic acid ester of the general formula [2].

In the second step, the reaction temperature can be lowered by reacting the target substrate with the acidic aqueous solution.

The reaction temperature is generally 150° C. or lower, preferably 135 to 0° C., more preferably 120 to 15° C.

The reaction time is generally 48 hours or less. Since the reaction time varies depending on the substrate material and the reaction conditions, it is preferable to determine the time at which there is seen almost no decrease of the substrate material as the end of the reaction while monitoring the progress of the reaction by any analytical means such as gas chromatography, liquid chromatography or nuclear magnetic resonance.

It is feasible to obtain the 3,3-difluoro-1,1-dichloro-2-propanone of the formula [3] by post-treatment operation commonly used in organic synthesis. The thus-recovered crude product can be purified to a higher purity, as required, by fractional distillation, recrystallization, column chromatography etc. When the reaction is performed in the presence of water, the 3,3-difluoro-1,1-dichloro-2-propanone of the formula [3] may be obtained as a hydrate (formula [3a]). The 3,3-difluoro-1,1-dichloro-2-propanone hydrate (gem-diol) of the formula [3a] can be easily converted to the 3,3-difluoro-1,1-dichloro-2-propanone (carbonyl compound) by dehydration, distillation etc. This hydrate may be used as the substrate material for the subsequent step in the same manner as the anhydride. Thus, the present invention includes the case where the hydrate compound of the formula [3a] is contained in the reaction product. When the reaction is performed without the use of the reaction solvent, it is convenient to recover the product compound directly from the reaction-completed solution by distillation.

3. Third Step (Alkali Decomposition Step)

In the third step, the 3,3-difluoro-2-hydroxypropionic acid of the formula [4] is formed by reacting the 3,3-difluoro-1,1-dichloro-2-propanone of the formula [3] obtained in the above second degradation step with the basic aqueous solution.

The basic aqueous solution is prepared from a base and water. Water remaining in the product of the previous step can be utilized as the water in this step.

Examples of the base are lithium hydrogencarbonate, sodium hydrogencarbonate, potassium hydrogencarbonate, lithium carbonate, sodium carbonate, potassium carbonate, lithium hydroxide, sodium hydroxide and potassium hydroxide. Among others, lithium carbonate, sodium carbonate, potassium carbonate, lithium hydroxide, sodium hydroxide and potassium hydroxide are preferred. Particularly preferred are lithium hydroxide, sodium hydroxide and potassium hydroxide. These bases can be used solely or in combination thereof.

The amount of the base used is generally 1.4 mol or more, preferably 1.6 to 20 mol, more preferably 1.8 to 10 mol, per 1 mol of the 3,3-difluoro-1,1-dichloro-2-propanone of the formula [3].

The concentration of the basic aqueous solution is generally 0.3% or higher, preferably 0.5 to 90%, more preferably 0.7 to 80%.

In the third step, the reaction can be performed at a pH of 9 or higher. The pH of the reaction system is preferably 10 to 14, more preferably 11 to 14. It is preferable to perform the reaction while monitoring the pH and adjusting the pH to within a preferable range.

Examples of the reaction solvent are alcohol solvents such as methanol, ethanol, n-propanol, n-butanol, isobutanol, tert-butanol and n-pentanol. Among others, methanol, ethanol, n-propanol and n-butanol are preferred. Particularly preferred are methanol and ethanol. These reaction solvents can be used solely or in combination thereof. In the second step, the reaction can be performed without the use of the reaction solvents. In some cases, it may be preferable to perform the reaction in a neat condition.

The amount of the reaction solvent used is generally 0.01 L or more, preferably 0.02 to 7 L, more preferably 0.03 to 5 L, per 1 mol of the 3,3-difluoro-1,1-dichloro-2-propanone of the formula [3].

The reaction temperature is generally +100° C. or lower, preferably +75 to −30° C., more preferably +50 to −15° C.

The reaction time is generally 36 hours or less. Since the reaction time varies depending on the substrate material and the reaction conditions, it is preferable to determine the time at which there is seen almost no decrease of the substrate material as the end of the reaction while monitoring the progress of the reaction by any analytical means such as gas chromatography, liquid chromatography or nuclear magnetic resonance.

It is feasible to obtain the 3,3-difluoro-2-hydroxypropionic acid of the formula [4] by post-treatment operation commonly used in organic synthesis. The target compound is present in the form of an alkali metal salt in the reaction-completed solution. Thus, the target compound can be obtained by neutralizing the reaction-completed solution with an inorganic acid such as hydrochloric acid or sulfuric acid, extracting the neutralized solution with an ester solvent such as ethyl acetate or n-butyl acetate, or an ether solvent such as tetrahydrofuran or tert-butyl methyl ether, and then, concentrating the extract under reduced pressure. The thus-recovered crude product can be purified to a higher purity, as required, by fractional distillation, recrystallization, column chromatography etc.

The above-obtained 3,3-difluoro-2-hydroxypropionic acid of the formula [4] can be easily converted to a 3,3-difluoro-2-hydroxypropionic amide as disclosed in Patent Document 1.

EXAMPLES

The present invention will be described in more detail below by way of the following examples. It should be understood that the following examples are not intended to limit the present invention thereto.

[Example 1] Chlorination of ethyl 4,4-difluoro-3-oxobutanoate (Using Chloroform as Reaction Solvent)

First, 4.8 g (68 mmol, 2.3 eq) of chlorine ($Cl_2$) was blown into a mixed solution of 5.0 g (30 mmol, 1.0 eq) of ethyl 4,4-difluoro-3-oxobutanoate and 21 mL (0.70 mL/mmol) of chloroform over 2 hours while the internal temperature of the reaction system was controlled to 0 to 5° C. Subsequently, nitrogen ($N_2$) was blown into the reaction-completed solution so as to purge the remaining chlorine gas. The reaction-completed solution was then analyzed by $^{19}$F-NMR analysis. It was confirmed that: the conversion rate was 96%; the molar ratio of ethyl 4,4-difluoro-2-chloro-3-oxobutanonate (carbonyl compound) and ethyl 4,4-difluoro-2,2-dichloro-3-oxobutanonate (carbonyl compound) was 65:35; and the efficiency of use of the chlorine was 57%.

[Example 2] Chlorination of ethyl 4,4-difluoro-3-oxobutanoate (in Neat Condition 1)

First, 43 g (0.61 mol, 2.0 eq) of chlorine ($Cl_2$) was blown into 50 g (0.30 mol, 1.0 eq) of ethyl 4,4-difluoro-3-oxobutanoate over 2 hours while the internal temperature of the reaction system was controlled to 0 to 5° C. Subsequently, nitrogen ($N_2$) was blown into the reaction-completed solution so as to purge the remaining chlorine gas. The reaction-completed solution was then analyzed by $^{19}$F-NMR analysis. It was confirmed that: the conversion rate was 97%; the molar ratio of ethyl 4,4-difluoro-2-chloro-3-oxobutanonate (carbonyl compound) and ethyl 4,4-difluoro-2,2-dichloro-3- oxobutanonate (carbonyl compound) was 94:6; and the efficiency of use of the chlorine was 51%.

[Example 3] Chlorination of ethyl 4,4-difluoro-3-oxobutanoate (in Neat Condition 2)

First, 170 g (2.4 mol, 8.0 eq) of chlorine ($Cl_2$) was blown into 50 g (0.30 mol, 1.0 eq) of ethyl 4,4-difluoro-3-oxobutanoate over 3 hours and 30 minutes while the internal temperature of the reaction system was controlled to 0 to 5° C. Subsequently, nitrogen ($N_2$) was blown into the reaction-completed solution so as to purge the remaining chlorine gas. The reaction-completed solution was then analyzed by $^{19}$F-NMR analysis. It was confirmed that: the conversion rate was 99%; the molar ratio of ethyl 4,4-difluoro-2-chloro-3-oxobutanonate (carbonyl compound) and ethyl 4,4-difluoro-2,2-dichloro-3-oxobutanonate (carbonyl compound) was 96:4; and the efficiency of use of the chlorine was 13%. Even though the chlorine was used in a large excess amount, there was observed no perchlorinated by-product.

[Example 4] Chlorination of ethyl 4,4-difluoro-3-oxobutanoate (in Neat Condition 3 in the Presence of Water)

First, 130 g (1.8 mol, 2.0 eq) of chlorine ($Cl_2$) was blown into a mixed solution of 150 g (0.90 mol, 1.0 eq) of ethyl 4,4-difluoro-3-oxobutanoate and 0.15 L (0.17 L/mol) of water over 8 hours and 30 minutes while the internal temperature of the reaction system was controlled to 0 to 5° C. Subsequently, nitrogen ($N_2$) was blown into the reaction-completed solution so as to purge the remaining chlorine gas. The reaction-completed solution was then analyzed by $^{19}$F-NMR analysis. It was confirmed that: the conversion rate was 87%; the molar ratio of ethyl 4,4-difluoro-2-chloro-3-oxobutanonate (gem-diol) and ethyl 4,4-difluoro-2,2-dichloro-3-oxobutanonate (gem-diol) was 28:72; and the efficiency of use of the chlorine was 75%.

[Example 5] Production of 3,3-difluoro-1,1-dichloro-2-propanone (in Neat Condition 4; Through-Experiment Allowing Monochlorination in Absence of Water and then Dichlorination in Presence of Water)

First, 0.22 kg (3.1 mol, 1.0 eq) of chlorine ($Cl_2$) was blown into 0.5 kg (3.0 mol, 1.0 eq) of ethyl 4,4-difluoro-3-oxobutanoate over 3 hours while the internal temperature of the reaction system was controlled to 0 to 5° C. Subsequently, nitrogen ($N_2$) was blown into the reaction mixture so as to purge the remaining chlorine gas. The reaction mixture was then analyzed by $^{19}$F-NMR analysis. It was confirmed that: the conversion rate was 93%; the molar ratio of ethyl 4,4-difluoro-2-chloro-3-oxobutanonate (carbonyl compound) and ethyl 4,4-difluoro-2,2-dichloro-3-oxobutanonate (carbonyl compound) was 92:8; and the efficiency of use of the chlorine was 98%.

To the reaction mixture, 1.2 L (0.40 L/mol) of water was added. After that, 0.22 kg (3.1 mol, 1.0 eq) of chlorine ($Cl_2$) was blown into the reaction mixture over 3 hours while the internal temperature of the reaction system was controlled to 0 to 5° C. Nitrogen ($N_2$) was subsequently blown into the reaction mixture so as to purge the remaining chlorine gas. The reaction mixture was then analyzed by $^{19}$F-NMR analysis. It was confirmed that: the conversion rate was 100%; the molar ratio of ethyl 4,4-difluoro-2-chloro-3-oxobutanonate (carbonyl compound) and ethyl 4,4-difluoro-2,2-dichloro-3-oxobutanonate (carbonyl compound) was 0:100; and the efficiency of use of the chlorine was 97%.

The reaction mixture was kept stored all night at room temperature, and then, again analyzed by $^{19}$F-NMR analysis. It was confirmed that: there was generated 3,3-difluoro-1,1-dichloro-2-propanone (gem-diol); and the molar ratio of ethyl 4,4-difluoro-2,2-dichloro-3-oxobutanoate (gem-diol) and 3,3-difluoro-1,1-dichloro-2-propanone (gem-diol) was 90:10. No perchlorinated by-product was observed under the preferable reaction conditions.

To the whole of 2.0 kg (regarded as 3.0 mol) of the reaction-completed solution obtained in the chlorination step, 1.6 kg (16 mol, 5.3 eq) of sulfuric acid was added. This reaction-completed solution was stirred for 15 hours at 100° C. and subjected to simple distillation (61° C./9.0 kPa), thereby obtaining 0.82 kg of an aqueous solution of 3,3-difluoro-1,1-dichloro-2-propanone (gem-diol). The distilled aqueous solution was quantified by $^{19}$F-NMR analysis (internal standard method). It was confirmed that: 0.52 kg (2.9 mol) of 3,3-difluoro-1,1-dichloro-2-propanone (gem-diol) was contained in the distilled aqueous solution; and the total quantitative yield of the two steps was 97%.

The whole of 0.82 kg (2.9 mol, 1.0 eq) of the distilled aqueous solution obtained in the degradation step was mixed with 1.3 kg (11 mol, 3.8 eq) of 35% aqueous sodium hydroxide solution while the internal temperature of the reaction system was controlled to 0 to 5° C. The mixed solution was stirred for 5 hours at the same temperature. (The pH of the mixed solution was 11 to 14.)

Further, the pH of the reaction-completed solution was adjusted to 1 to 2 by adding 5% hydrochloric acid to the reaction-completed solution while controlling the temperature of the reaction-completed solution to 0 to 5° C. Then, the reaction-completed solution was extracted with tetrahydrofuran. The recovered organic layer was concentrated under reduced pressure and dried under vacuum, thereby obtaining 0.30 kg (2.4 mol) of 3,3-difluoro-2-hydroxypropionic acid. The yield of this step was 83%. The total yield of the three steps was 80%.

As is apparent from the above results, it is possible in the chlorination step of the present invention to effectively suppress the generation of a perchloride as a by-product by adoption of the mild reaction temperature (see Examples 3 and 5). It is also possible to improve the efficiency of use of chlorine by reacting the target substrate with chlorine in the presence of water (see TABLE 1 and Example 4). In particular, it is possible to further improve the efficiency of use of chlorine by performing the monochlorination in the absence of water and then performing the dichlorination in the presence of water (see Example 5 in comparison with Example 2). For information, the efficiency of use of chlorine cannot be significantly improved even with the use of a halogenated reaction solvent used for ordinary chlorination in organic synthesis (see Example 1).

TABLE 1

| Example | Water | Reaction Solvent | Chlorine gas | Conversion rate | Monochlorination:dichlorination ratio | Efficiency of use |
|---------|-------|------------------|--------------|-----------------|----------------------------------------|-------------------|
| 1 | X | chloroform | 2.27 eq | 96% | 65:35 | 57% |
| 2 | X | neat | 2.03 eq | 97% | 94:6 | 51% |
| 3 | X | neat | 8.00 eq | 99% | 96:4 | 13% |
| 4 | ○ | neat | 2.00 eq | 87% | 28:72 | 75% |
| 5-1* | X | neat | 1.03 eq | 93% | 92:8 | 98% |
| 5-2* | ○ | neat | 2.07 eq | 100% | 0:100 | 97% |

*5-1: Monochlorination 5-2: Dichlorination

[Example 6] Conversion of 4,4-difluoro-2,2-dichloro-3-oxobutanonate (from Gem-Diol to Carbonyl Compound)

The experiment of Example 5 was retried using 170 g (1.0 mol) of ethyl 4,4-difluoro-3-oxobutanoate. The reaction-completed solution after the chlorination step, which contained ethyl 4,4-difluoro-2,2-dichloro-3-oxobutanoate (gem-diol), was extracted with diethyl ether. The recovered organic layer was concentrated under reduced pressure and subjected to fractional distillation (92° C./3.6 kPa), thereby obtaining 200 g (0.85 mol) of ethyl 4,4-difluoro-2,2-dichloro-3-oxobutanoate (carbonyl compound). The yield of the chlorination step was 85%.

[Example 7] Conversion of ethyl 4,4-difluoro-2,2-dichloro-3-oxobutanonate (carbonyl compound) to 3,3-difluoro-1,1-dichloro-2-propanone To 40 g (0.17 mol, 1.0 eq) of the ethyl 4,4-difluoro-2,2-dichloro-3-oxobutanoate (carbonyl compound) obtained in Example 6, 34 g (0.35 mol, 2.1 eq) of sulfuric acid was added. The resulting mixture was stirred for 2 hours at 150° C. Gas generated during the stirring was liquefied and recovered by cooling, thereby obtaining 17 g (0.10 mol) of 3,3-difluoro-1,1-dichloro-2-propanone (carbonyl compound). The yield of this step was 59%.

[Example 8] Conversion of 3,3-difluoro-1,1-dichloro-2-propanone (from Gem-Diol to Carbonyl Compound)

Into 40 g (410 mmol, 4.9 eq) of concentrated sulfuric acid heated to 130° C., 15 g (83 mmol, 1.0 eq) of 3,3-difluoro-1,1-dichloro-2-propanone (gem-diol) was slowly dropped while stirring for 1 hour. Gas generated during the stirring was liquefied and recovered by cooling, thereby obtaining 7.5 g (46 mmol) of 3,3-difluoro-1,1-dichloro-2-propanone (carbonyl compound). The yield of this step was 55%.

Example 9

Prepared was a mixed solution of 20 mg (0.12 mmol, 1.0 eq) of the 3,3-difluoro-1,1-dichloro-2-propanone (carbonyl compound) obtained in Example 7 and 0.5 mL (4.2 mL/mmol) of methanol. Further, 550 mg (1.3 mmol, 11 eq) of 9.1% aqueous sodium hydroxide solution was added to the mixed solution while the temperature of the mixed solution was controlled to 0 to 5° C. The mixed solution was reacted by stirring for 2 hours and 15 minutes at the same temperature. The pH of the reaction-completed solution was adjusted to 1 to 2 by adding 3N hydrochloric acid to the reaction-completed solution while controlling the temperature of the reaction-completed solution to 25° C. or lower. Then, the reaction-completed solution was extracted with ethyl acetate. The recovered organic layer was concentrated under reduced pressure and dried under vacuum, thereby obtaining 15 mg (0.12 mmol) of 3,3-difluoro-2-hydroxypropionic acid. The yield of this step was quantitative.

[Example 10] Degradation of ethyl 4,4-difluoro-2,2-dichloro-3-oxobutanoate (Gem-Diol) (Under Mild Reaction Condition 1)

The experiment of Example 5 was retried using 0.96 kg (5.8 mol) of ethyl 4,4-difluoro-3-oxobutanoate. To 3.7 kg (1.0 eq, water content: 2.2 kg) of the reaction-completed solution after the chlorination step, which contained 1.5 kg (5.8 mol) of ethyl 4,4-difluoro-2,2-dichloro-3-oxobutanoate (gem-diol), 58 g (0.56 mol, 0.097 eq) of 95% sulfuric acid was added. The reaction-completed solution was then stirred for 18 hours at 98° C. The reaction-completed solution was quantified by $^{19}$F-NMR analysis (internal standard method). It was confirmed that 0.92 kg (5.1 mol) of 3,3-difluoro-1,1-dichloro-2-propanone (gem-diol) was contained in the reaction-completed solution. The quantitative yield of this step was 88%.

[Example 11] Degradation of ethyl 4,4-difluoro-2,2-dichloro-3-oxobutanoate (Gem-Diol) (Under Mild Reaction Condition 2)

In the same manner as in Example 10, 37 g (1.0 eq, water content: 22 g) of the reaction-completed solution after the chlorination step, which contained 15 g (58 mmol) of ethyl 4,4-difluoro-2,2-dichloro-3-oxobutanoate (gem-diol), was mixed with 0.60 g (6.1 mmol, 0.11 eq) of sulfuric acid and then stirred for 20 hours at 68° C. The reaction-completed solution was quantified by 19F-NMR analysis (internal standard method). It was confirmed that 5.2 g (29 mmol) of 3,3-difluoro-1,1-dichloro-2-propanone (gem-diol) was contained in the reaction-completed solution. The quantitative yield of this step was 50%.

[Example 12] Degradation of ethyl 4,4-difluoro-2,2-dichloro-3-oxobutanoate (Gem-Diol) (Under Mild Reaction Condition 3)

In the same manner as in Example 10, 37 g (1.0 eq, water content: 22 g) of the reaction-completed solution after the chlorination step, which contained 15 g (58 mmol) of ethyl 4,4-difluoro-2,2-dichloro-3-oxobutanoate (gem-diol), was stirred for 20 hours at 67° C. The reaction-completed solution was quantified by $^{19}$F-NMR analysis (internal standard method). It was confirmed that 5.8 g (32 mmol) of 3,3-difluoro-1,1-dichloro-2-propanone (gem-diol) was contained in the reaction-completed solution. The quantitative yield of this step was 55%. This step proceeded even with the use of hydrogen chloride remaining in the product of the previous step.

[Reference Example 1] Conversion to 3,3-difluoro-2-hydroxypropionic amide (via methyl 3,3-difluoro-2-hydroxypropionate)

To a mixed solution of 330 g (2.6 mol, 1.0 eq) of 3,3-difluoro-2-hydroxypropionic acid and 84 g (2.6 mol, 1.0 eq) of methanol, 280 g (2.6 mol, 1.0 eq) of trimethyl orthoformate and 27 g (0.28 mol, 0.11 eq) of sulfuric acid were added. The resulting solution was stirred for 17 hours under reflux. The reaction-completed solution was subjected to simple distillation (~50° C./0.1 kPa), thereby obtaining 330 g (2.4 mol) of methyl 3,3-difluoro-2-hydroxypropionate. The yield of this conversion reaction was 92%.

Subsequently, 3.6 g (210 mmol, 38 eq) of ammonia gas ($NH_3$) was blown into a mixed solution of 0.78 g (5.6 mmol, 1.0 eq) of the obtained methyl 3,3-difluoro-2-hydroxypropionate and 30 mL (5.4 mL/mol) of methanol while the internal temperature of the reaction system was controlled to 0 to 5° C. The mixed solution was then stirred for 2 hours at 50° C. The reaction-completed solution was quantified by $^{19}$F-NMR analysis (internal standard method). It was confirmed that 550 mg (4.4 mmol) of 33,3-difluoro-2-hydroxypropionic amide was contained in the reaction-completed solution. The quantitative yield of this conversion reaction was 79%.

The $^1$H-NMR and $^{19}$F-NMR data of the products of Examples and Reference Example are indicated below.

Ethyl 4,4-difluoro-2-chloro-3-oxobutanoate (Carbonyl Compound)

$^1$H-NMR (reference material: tetramethylsilane, solvent: deuterated chloroform) δ ppm; 1.30 (t, 3H), 4.31 (q, 2H), 5.22 (s, 1H), 6.12 (t, 1H).
$^{19}$F-NMR (reference material: hexafluorobenzene, solvent: deuterated chloroform) δ ppm; 35.25 (d, 2F).

Ethyl 4,4-difluoro-2-chloro-3-oxobutanoate (Gem-Diol)

$^{19}$F-NMR (reference material: hexafluorobenzene, solvent: deuterated chloroform) δ ppm; 26.42 (dd, 1F), 29.80 (dd, 1F).

Ethyl 4,4-difluoro-2,2-dichloro-3-oxobutanoate (Carbonyl Compound)

$^1$H-NMR (reference material: tetramethylsilane, solvent: deuterated chloroform) δ ppm; 1.28 (t, 3H), 4.34 (q, 2H), 6.26 (t, 1H).
$^{19}$F-NMR (reference material: hexafluorobenzene, solvent: deuterated chloroform) δ ppm; 37.54 (d, 2F).

Ethyl 4,4-difluoro-2,2-dichloro-3-oxobutanoate (Gem-Diol)

$^{19}$F-NMR (reference material: hexafluorobenzene, solvent: deuterated water) δ ppm; 32.27 (d, 2F).

3,3-Difluoro-1,1-dichloro-2-propanone (Carbonyl Compound)

$^1$H-NMR (reference material: tetramethylsilane, solvent: deuterated chloroform) δ ppm; 6.31 (t, 1H), 6.34 (s, 1H).
$^{19}$F-NMR (reference material: hexafluorobenzene, solvent: deuterated chloroform) δ ppm; 34.91 (d, 2F).

3,3-Difluoro-1,1-dichloro-2-propanone (Gem-Diol)

$^1$H-NMR (reference material: tetramethylsilane, solvent: deuterated acetone) δ ppm; 6.02 (s, 1H), 6.08 (t, 1H). Two protons of gem-diol were unidentified.
$^{19}$F-NMR (reference material: hexafluorobenzene, solvent: deuterated chloroform) δ ppm; 28.25 (d, 2F).

3,3-Difluoro-2-hydroxypropionic acid $^1$H-NMR (reference material: tetramethylsilane, solvent: deuterated dimethyl sulfoxide) δ ppm; 4.32 (m, 1H), 6.14 (m, 1H). Protons of hydroxyl and carboxyl groups were unidentified.
$^{19}$F-NMR (reference material: hexafluorobenzene, solvent: deuterated dimethyl sulfoxide) δ ppm; 31.90 (m, 1F), 35.29 (m, 1F).

Methyl 3,3-difluoro-2-hydroxypropionate $^1$H-NMR (reference material: tetramethylsilane, solvent: deuterated chloroform) δ ppm; 3.58 (s, 11H), 3.88 (s, 3H), 4.43 (m, 1H), 5.98 (m, 1H).
$^{19}$F-NMR (reference material: hexafluorobenzene, solvent: deuterated chloroform) δ ppm; 31.36 (m, 1F), 32.88 (m, 1F).

3,3-Difluoro-2-Hydroxypropionic amide $^{19}$F-NMR (reference material: hexafluorobenzene, solvent: deuterated methanol) δ ppm; 30.59 (m, 1F), 34.37 (m, 1F).

INDUSTRIAL APPLICABILITY

The target compound of the present invention, that is, 3,3-difluoro-2-hydroxypropionic acid is useful as pharmaceutical and agrichemical intermediates.

The invention claimed is:
1. A method for producing 3,3-difluoro-2-hydroxypropionic acid of the formula [4]

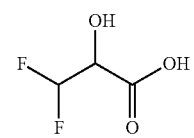

[4]

the method comprising the following steps:
[first step] reacting a 4,4-difluoro-3-oxobutanoic acid ester of the general formula [1] with chlorine, thereby forming a 4,4-difluoro-2,2-dichloro-3-oxobutanoic acid ester of the general formula [2]

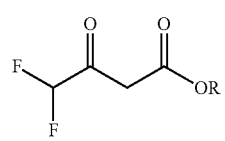

[1]

where R is a $C_1$-$C_6$ alkyl group;

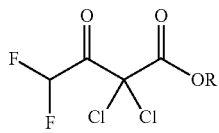
[2]

where R is a $C_1$-$C_6$ alkyl group;

[second step] reacting the 4,4-difluoro-2,2-dichloro-3-oxobutanoic acid ester with an acid, thereby forming 3,3-difluoro-1,1-dichloro-2-propanone of the formula [3]

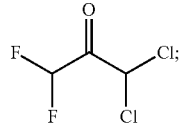
[3]

and

[third step] reacting the 3,3-difluoro-1,1-dichloro-2-propanone with a basic aqueous solution to obtain the 3,3-difluoro-2-hydroxypropionic acid of the formula [4]

wherein the first step includes: converting the 4,4-difluoro-3-oxobutanoic acid ester of the general formula [1] to a 4,4-difluoro-2-chloro-3-oxobutanoic acid ester of the general formula [5] by reaction with chlorine in the absence of water; and then, converting the 4,4-difluoro-2-chloro-3-oxobutanoic acid ester to the 4,4-difluoro-2,2-dichloro-3-oxobutanoic acid ester of the general formula [2] by reaction with chlorine in the presence of water

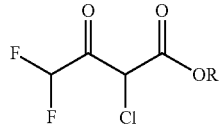
[5]

where R is a $C_1$-$C_6$ alkyl group.

2. The method according to claim 1, wherein the acid used in the second step is an acidic aqueous solution.

3. The method according to claim 1, wherein the first step is performed at a reaction temperature of +50 to −30° C.

4. The method according to claim 2, wherein the acidic aqueous solution has a concentration of 0.3 to 90%.

5. The method according to claim 2, wherein the acid reacted with the 4,4-difluoro-2,2-dichloro-3-oxobutanoic acid ester in the second step is hydrogen chloride remaining the 4,4-difluoro-2,2-dichloro-3-oxobutanoic acid ester after the first step.

6. The method according to claim 1, wherein the second step is performed at a reaction temperature of +135 to 0° C.

* * * * *